United States Patent
Reisch

(12) 
(10) Patent No.: US 6,916,491 B2
(45) Date of Patent: Jul. 12, 2005

(54) FUNGUS INHIBITING BIOLOGICAL COMPOUND

(76) Inventor: Dennis Reisch, 10 Clark Rd., Pasco, WA (US) 99301

( * ) Notice: Subject to any disclaimer, the term of this patent is extended or adjusted under 35 U.S.C. 154(b) by 0 days.

(21) Appl. No.: 10/132,952

(22) Filed: Apr. 26, 2002

(65) Prior Publication Data

US 2003/0203041 A1 Oct. 30, 2003

(51) Int. Cl.$^7$ .......................... A01N 63/00; A61K 35/00
(52) U.S. Cl. ........................................ 424/535; 424/93.4
(58) Field of Search ................ 424/535, 93.4, 424/439, 404, 405, 400

(56) References Cited

U.S. PATENT DOCUMENTS

| | | | | |
|---|---|---|---|---|
| 4,842,871 A | * | 6/1989 | Hill | 426/44 |
| 4,851,445 A | * | 7/1989 | Yoshimoto et al. | 514/604 |
| 2002/0025928 A1 | * | 2/2002 | Forssmann et al. | 514/12 |

FOREIGN PATENT DOCUMENTS

JP  404041833 A  * 2/1992

OTHER PUBLICATIONS

DW 1997–469499, Sep. 1997, Derwent, Zanin.*
DW 1992–418102, Nov. 1992, Derwent, Central Glass Co. LTD.*

* cited by examiner

*Primary Examiner*—Bruce R. Campbell
*Assistant Examiner*—Randall Winston
(74) *Attorney, Agent, or Firm*—Floyd E. Ivey; Liebler, Ivey, Connor, Berry & St. Hilaire

(57) ABSTRACT

A method of producing a biological fungicide composed of milk products, namely powdered cow milk, cow milk culture or bacteria culture, and a calcium carbonate. These components can be mixed to form a mixture, stored for long-term at below 32 degrees Fahrenheit or held below 75 degrees Fahrenheit for one month. Upon application of the mixture, fulvic acid may be added to the mixture.

13 Claims, No Drawings

FUNGUS INHIBITING BIOLOGICAL COMPOUND

BACKGROUND OF THE INVENTION

1. Field of the Invention

The present invention relates to a fungus inhibiting biological compound and, more particularly, to a biological fungicide for tree, vine, row crops, ornamentals and green house cultivars.

2. Brief Description of Related Developments

For many centuries various chemicals have been applied to control plant diseases. One category of plant diseases that has plagued farmers through time is fungi or funguses.

Fungi are any group of nonphotosynthetic organisms feeding on organic matter. Although fungi are particularly famous for their attack and destruction of potatoes (e.g., the great Irish potato famines), fungi also readily attack every agricultural crop known including but without limitation, for example, tree and vine crops, grains, grasses, grapes, hops; row crops, including snap beans, corn, carrots, onions, and melons; ornamentals; green house cultivars and all other agricultural crops and plants.

In order to protect crops from the destructive nature of fungi, a wide variety of chemicals have been used in fungicides. A partial list of the chemicals that have been used in fungicides is as follows: lime, mercury, copper, iron, zinc, manganese, quinones, and dicarboximides. All of these chemicals have an impact on the environment; they leach into the fresh water supply as contaminants and may even damage the crops that have the fungus.

Therefore, an environmentally safe solution to the above problems has been sought and found in milk products.

SUMMARY OF THE INVENTION

The present invention is directed to a fungus inhibiting biological compound comprising milk products. In one embodiment, the biological fungicide comprises, a powdered cow milk; a cow milk culture; and a calcium carbonate.

In one aspect, the present invention is directed to the manufacturing of a biological fungicide. In one manufacturing embodiment, the method of manufacturing a biological fungicide comprises the steps of: producing a dried cow milk; producing a culture; producing a calcium carbonate; and mixing the dried cow milk, the culture and the calcium carbonate to form a mixture.

In a second manufacturing embodiment, the method of manufacturing a biological fungicide, comprises the steps of: producing a dried cow milk; producing a culture; producing a calcium carbonate; producing a sugar; mixing the dried cow milk, the culture, the calcium carbonate, and the sugar to form a mixture; freezing the mixture; shipping the frozen mixture to an application site; allowing the frozen mixture to thaw; and adding a fulvic acid to the thawed mixture to form a complete mixture.

In another aspect, the present invention is directed to the use or application of a biological fungicide solution. In one use embodiment, a method of using a biological fungicide solution on tree and vine crops to inhibit fungus, comprises the steps of: allowing a crop infested with fungus to reach at least three-quarter leaf; adding five pounds of a biological fungicide compound to one-hundred gallons of water and between 10 ounces and 15 ounces of fulvic acid, to form a mixture; agitating the mixture to form a biological fungicide solution; and spraying the fungicide solution on an acre of the crop to provide complete coverage.

In a second use embodiment, a method of using a biological fungicide solution to inhibit fungus on row crops, comprises the steps of: adding five pounds of the biological fungicide compound to twenty gallons of water and 16 ounces of fulvic acid, to form a mixture; agitating the mixture to form a biological fungicide solution; and spraying the biological fungicide solution on an acre of a row crop to provide complete coverage.

In yet another aspect, the present invention is directed to the storage or preservation of a biological fungicide. In one storage embodiment, the method of preserving the biological fungicide compound, comprises the steps of: placing the biological fungicide compound in a freezable container; and holding the temperature of the biological fungicide compound below 32 degrees Fahrenheit until mixing with fulvic acid, diluting with a volume of water and applying.

DETAILED DESCRIPTION OF THE PREFERRED EMBODIMENTS

Within the recent past, the inventor was challenged to derive a fungicide for hops. Initially, the inventor applied a cow milk and water combination to a crop of hops contaminated with a fungus. There were no marked positive results.

Second, the inventor applied a combination of cow milk and cottage cheese, made from cow milk, to a crop of hops contaminated with a fungus. This application had mixed results. Some of the fungus was eradicated. These results allowed the inventor to realize that the bacteria in the cottage cheese were at least some of the active ingredients that attacked the fungus. However, upon commercial application the percentage of the fungus eradicated decreased.

This second attempt led the inventor to conclude that an increase in the pH of the mixture would increase the activity of the bacteria in the mixture. One method used to accomplish this goal was to mix a calcium carbonate in with the milk and cottage cheese. Coincidental with this idea came the thought that a small amount of fulvic acid included in the mix would augment the amount leaf penetration by the active bacteria. The form of fulvic acid used in this second attempt was K-TONIC™. K-TIONIC™ serves much like a fertilizer adjuvant that allows for a greater nutrient uptake through roots and leaves. The results of this third attempt with the new mixture were notable.

The most prominent component in the biological fungicide compound is milk. Milk is a complete food for the new born. It contains water, fat, protein, carbohydrate, ash, calcium, and phosphorus. It is commercially produced from goats, reindeer, donkeys, yaks, water buffalo, sheep, camels, mares, and cows. One of the most economical and plentiful sources of milk are dairy cows.

The composition of milk from dairy cows can be altered by a number of factors such as breed, age, health of the cow, the season of the year, and time lapse between milking (Encyclopedia Americana, Int'l ed., 19, at 113 (1998)). Therefore, the percentages of the components of milk will vary. The general composition of dry whole milk is as follows: 2.5% water, 26.7% fat, 26.3% protein, 38.4% carbohydrate (lactose), 6.1% ash, and 912 mg/100 g calcium and 776 mg/100 g phosphorus. (Compton's Encyclopedia & Fact Index, 15 at 414 (2002)). The commercially produced dried milk used in the preferred biological fungicide compound is DARIX® GR-A NFDM LH which will be recognized by those of ordinary skill in the industry as Darigold Grade A Non-Fat Milk Low Heat. However, as shown in this discussion any kind and any source of milk could be used to make this biological fungicide.

The second main component to the biological fungicide compound is a calcium carbonate. A calcium carbonate can be purchased from a variety of sources on the national or international market. One type that has been successfully used is Mississippi HO-M60, milled, and precipitated calcium carbonates. Any source could be used so long as the product has sufficient purity not to contaminate the biological fungicide.

The third component to the biological fungicide compound is a bacteria culture. Several bacteria are used in cow milk products as mother or starter cultures such as *Streptococcus lactis, Streptococcus cremoris, Streptococcus diacetilactis, Streptococcus thermophilus, Leuconostoc cremoris, Lactobacillus acidophilis* and *Lactobacillus bulgaricus.* (McGraw-Hill Encyclopedia of Science & Technology, p. 250 (1997)).

A wide variety of cultured cow milk products could be used in this biological fungicide compound such as cottage cheese, yogurt (*Streptococcus thermophilus* and *Lactobacillus bulgaricus*), sour cream, buttermilk (*Streptococcus lactis* and *Leuconostoc cremoris*). Drawing from the cultured cow milk products produced internationally, one skilled in the art could use any number fermented milk products for the bacteria culture in the biological fungicide.

The particular cultures used in the biological fungicide compound are a heterotrophic plate and/or some lactobacillus. In the initial uses of cottage cheese in the biological fungicide, there was a bacteria count of approximately 100,000/gram that was applied at about 34,000,000 bacteria/acre. This concentration was sought to be duplicated in the application of the commercial culture of SH-1 at about 36,000,000 bacteria/acre.

The fourth component in the biological fungicide compound is fulvic acid. Fulvic acid is an organic complex; it is characterized by molecular weights between 3,000 and 20,000 grs./mol. that are formed by the decomposition of organic matter. K-TIONIC™ is a commercially prepared and sold fulvic organic complex that is derived from leonardite and fulvic substances of organic origin.

The general volume percentage of the biological fungicide compound is as follows: 91.61% dried cow milk, 4.39% calcium carbonate, 3.98% cow milk culture, and 0.02% sugar. The volume percentages of the components of the biological fungicide compound can be varied. A calcium carbonate can have a volume percentage from 2.99 to 6.99; sugar can have a volume percentage from 0 to 5; and fulvic acid can have a volume percentage from 0.33 to 25.

The application of the biological fungicide compound is calculated in pounds per acre. The general application in pounds per acre is as follows: dried cow milk 4.600 lbs/acre, calcium carbonate 0.220 lbs/acre, cow milk culture 0.200 lbs/acre, and sugar 0.001 lbs/acre. In order to apply the biological fungicide compound to crops, the compound is mixed or diluted with water and a few ounces of fulvic acid to form the biological fungicide solution for application.

The mixing or agitation of the biological fungicide solution can be accomplished by a wide variety of methods. One method may be to fill a spray tank one-third to one-half full of water with the agitator in operation. While the agitator is left in operation the biological fungicide compound and fulvic acid are then added, the tank is then filled with water and the biological fungicide solution is applied until the tank is empty and the process of mixing and application is repeated as necessary.

Preservation or storage of the biological fungicide compound can be performed, in at least two methods. First, by keeping the compound below 75 degrees Fahrenheit for one month, the compound still has a heterotrophic plate count of $9 \times 10^2$ and a lactobacillus count of $<1 \times 10^2$. Although, there is a marked decrease from the original respective counts of $1.1 \times 10^6$ and $6.6 \times 10^4$, these counts show that the active bacteria could still be used for application in the compound. Second, the biological fungicide compound may be preserved for an almost indefinite period of time by freezing the biological fungicide at below 32 degrees Fahrenheit. Using this method of preservation the compound may be shipped frozen and stored frozen until the time for application or the compound may be shipped and allowed to thaw in transit for prompt application upon arrival.

The application of the biological fungicide compound has been found useful for a wide variety of crops. Some specific methods of use are as follows.

First, for tree and vine crops, five (5) pounds of the biological fungicide compound is applied by mixing with 100 gallons of water in combination with 10 to 15 ounces of K-TIONIC™, a fulvic acid organic complex. The first application would be after training in hops or three-quarter leaf in orchards and vineyards, repeating the application at each fourteen-day interval. The biological fungicide solution is applied in sufficient quantity to provide a complete coverage of the crop. Second, for potatoes and any row crop such as snap beans, corn, carrots, onions or melons, five (5) pounds of the biological fungicide compound is applied per acre in minimum of twenty (20) gallons of water in combination with sixteen (16) ounces of K-TIONIC™ as needed. For potatoes, the first application should be just prior to row close of the potato plants, with repeat applications as needed.

As one skilled in the art would know there may be a much wider variety of trees, vines, and plants that would benefit from the application of the biological fungicide compound. It may also be found that different proportions of the compound, water, and K-TIONIC™ may be beneficial to particular trees, vines, and plants, than those proportions stated above.

The method of application of the biological fungicide compound to trees, vine, and row crops may be through the use of a hand held sprayer, a mechanical sprayer, a pneumatic sprayer, or an aerial sprayer. With a crop such as melons aerial application is not recommended.

It should be understood that the foregoing description is only illustrative of the invention. Various alternatives and modifications can be devised by those skilled in the art without departing from the invention. Accordingly, the present invention is intended to embrace all such alternatives, modifications and variances that fall within the scope of the appended claims.

I claim:

1. A biological fungicide, for the treatment of agricultural crops comprising:
    an effective amount of powdered milk;
    an effective amount of bacteria culture consisting of a heterotrophic plate and or a bacteria from milk products as mother or starter cultures of *Streptococcus lactis, Streptococcus cremoris, Streptococcus diacetilactis, Streptococcus thermophilus, Leuconestoc cremoris, Lactobacillus acidophilis* or *Lactobacillus bulgaricus*; and
    an effective amount of calcium carbonate.

2. The fungicide according to claim 1, further comprising, an effective amount of fulvic acid or a sugar.

3. The fungicide according to claim 2, wherein the effective amount of fulvic acid is between 0.33 and 25 of a volume percentage of the fungicide.

4. The fungicide according to claim 2, wherein the powdered milk is cow milk.

5. The fungicide according to claim 2, wherein the bacteria culture is *Lactobacillus acidophilis* or *Lactobacillus bulgaricus*.

6. The fungicide according to claim 2, wherein the bacteria culture is heterotrophic plate.

7. The fungicide according to claim 2, wherein the fungicide comprises a 100 volume percentage of, the effective amount of powdered cow milk, the effective amount of bacteria culture, the effective amount of calcium carbonate, and a sugar.

8. The fungicide according to claim 7, wherein the effective amount of powdered milk comprises 91.61 of the 100 volume percentage of the fungicide.

9. The fungicide according to claim 7, wherein the effective amount of calcium carbonate comprises a 4.39 of the 100 volume percentage of the fungicide.

10. The fungicide according to claim 7, wherein the effective amount of calcium carbonate is between 2.99 and 6.99 of the 100 volume percentage of the fungicide.

11. The fungicide according to claim 7, wherein the effective amount of bacteria culture comprises 3.98 of the 100 volume percentage of the fungicide.

12. The fungicide according to claim 7, wherein the sugar comprises 0.02 of the 100 volume percentage of the fungicide.

13. The fungicide according to claim 7, wherein the sugar comprises between 0.01 and 5 volume percentage of the fungicide.

* * * * *